US009789225B2

(12) United States Patent
Bagga et al.

(10) Patent No.: US 9,789,225 B2
(45) Date of Patent: *Oct. 17, 2017

(54) SHAPEABLE BONE GRAFT SUBSTITUTE AND INSTRUMENTS FOR DELIVERY THEREOF

(71) Applicant: Orthovita, Inc., Malvern, PA (US)

(72) Inventors: Charanpreet S. Bagga, Basking Ridge, NJ (US); Theodore D. Clineff, Phoenixville, PA (US); Erik M. Erbe, Chesterfield, MO (US); Michael W. Paris, Lansdale, PA (US); Gina M. Nagvajara, Narberth, PA (US); Antony Koblish, Malvern, PA (US)

(73) Assignee: Orthovita, Inc., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/933,217

(22) Filed: Nov. 5, 2015

(65) Prior Publication Data

US 2016/0051732 A1 Feb. 25, 2016

Related U.S. Application Data

(62) Division of application No. 10/874,994, filed on Jun. 23, 2004, now Pat. No. 9,220,595.

(51) Int. Cl.
| | | |
|---|---|---|
| *A61F 2/00* | (2006.01) | |
| *A61L 27/54* | (2006.01) | |
| *A61B 17/68* | (2006.01) | |
| *A61B 17/70* | (2006.01) | |
| *A61B 17/88* | (2006.01) | |
| *A61F 2/28* | (2006.01) | |
| *A61L 27/46* | (2006.01) | |
| *A61L 27/50* | (2006.01) | |
| *A61L 27/56* | (2006.01) | |
| *A61L 27/58* | (2006.01) | |
| *A61L 27/20* | (2006.01) | |
| *A61F 2/30* | (2006.01) | |
| *A61F 2/34* | (2006.01) | |
| *A61F 2/38* | (2006.01) | |
| *A61F 2/46* | (2006.01) | |

(52) U.S. Cl.
CPC .............. *A61L 27/54* (2013.01); *A61B 17/68* (2013.01); *A61B 17/7095* (2013.01); *A61B 17/8822* (2013.01); *A61F 2/28* (2013.01); *A61L 27/20* (2013.01); *A61L 27/46* (2013.01); *A61L 27/50* (2013.01); *A61L 27/56* (2013.01); *A61L 27/58* (2013.01); *A61F 2/2803* (2013.01); *A61F 2/2875* (2013.01); *A61F 2/3094* (2013.01); *A61F 2/34* (2013.01); *A61F 2/389* (2013.01); *A61F 2/4601* (2013.01); *A61F 2/4644* (2013.01); *A61F 2002/2817* (2013.01); *A61F 2002/2835* (2013.01); *A61F 2002/2882* (2013.01); *A61F 2002/30062* (2013.01); *A61F 2002/30151* (2013.01); *A61F 2002/30224* (2013.01); *A61F 2002/30235* (2013.01); *A61F 2002/30247* (2013.01); *A61F 2002/30261* (2013.01); *A61F 2002/30622* (2013.01); *A61F 2002/30677* (2013.01); *A61F 2002/30736* (2013.01); *A61F 2002/30838* (2013.01); *A61F 2210/0004* (2013.01); *A61F 2210/0085* (2013.01); *A61F 2230/0017* (2013.01); *A61F 2230/0069* (2013.01); *A61F 2230/0071* (2013.01); *A61F 2230/0082* (2013.01); *A61F 2310/00293* (2013.01); *A61F 2310/00365* (2013.01); *A61L 2400/06* (2013.01); *A61L 2400/16* (2013.01); *A61L 2430/02* (2013.01)

(58) Field of Classification Search
None
See application file for complete search history.

(56) References Cited

U.S. PATENT DOCUMENTS

| | | |
|---|---|---|
| 2,920,971 A | 1/1960 | Stookey |
| 3,090,094 A | 5/1963 | Schwartzwalder et al. |
| 3,443,261 A | 5/1969 | Battista et al. |
| 3,679,360 A | 7/1972 | Rubin et al. |
| 3,833,386 A | 9/1974 | Wood et al. |
| 3,877,973 A | 4/1975 | Ravault |
| 3,907,579 A | 9/1975 | Ravault |
| 3,981,736 A | 9/1976 | Broemer et al. |
| 4,004,933 A | 1/1977 | Ravault |
| 4,007,020 A | 2/1977 | Church et al. |
| 4,045,238 A | 8/1977 | Battista et al. |
| 4,149,893 A | 4/1979 | Aoki et al. |
| 4,149,983 A | 4/1979 | Grier et al. |
| 4,273,131 A | 6/1981 | Olsen |

(Continued)

FOREIGN PATENT DOCUMENTS

| | | |
|---|---|---|
| CA | 2278176 | 7/1998 |
| CA | 2398517 | 8/2001 |
| DE | 2208236 A1 | 9/1972 |
| EP | 0197693 A2 | 10/1986 |
| EP | 0263489 A1 | 4/1988 |
| EP | 0417493 A2 | 3/1991 |
| FR | 2664501 A1 | 1/1992 |
| GB | 2260538 A | 4/1993 |
| JP | 61201612 A | 9/1986 |

(Continued)

OTHER PUBLICATIONS

Tampieri et al., Posority-graded hydroxyapatite ceramics to replace natural bone, Biomaterial, 2001, vol. 22, pp. 1365-1370.

(Continued)

*Primary Examiner* — Jared D Barsky
(74) *Attorney, Agent, or Firm* — Lerner, David, Littenberg, Krumholz & Mentlik, LLP

(57) ABSTRACT

Injectable bone graft material having a biocompatible, resorbable polymer and a biocompatible, resorbable inorganic material exhibiting macro, meso, and microporosities.

16 Claims, 11 Drawing Sheets

(56) References Cited

U.S. PATENT DOCUMENTS

| | | | |
|---|---|---|---|
| 4,328,034 A | 5/1982 | Ferguson |
| 4,457,028 A | 7/1984 | Draenert |
| 4,491,453 A | 1/1985 | Koblitz et al. |
| 4,491,517 A | 1/1985 | Janovac |
| 4,563,350 A | 1/1986 | Nathan et al. |
| 4,604,097 A | 8/1986 | Graves, Jr. et al. |
| 4,609,923 A | 9/1986 | Boan et al. |
| 4,612,053 A | 9/1986 | Brown et al. |
| 4,613,627 A | 9/1986 | Sherman et al. |
| 4,619,655 A | 10/1986 | Hanker et al. |
| 4,643,982 A | 2/1987 | Kasuga et al. |
| 4,648,124 A | 3/1987 | Mantovani et al. |
| 4,652,459 A | 3/1987 | Engelhardt |
| 4,652,534 A | 3/1987 | Kasuga |
| 4,673,355 A | 6/1987 | Farris et al. |
| 4,693,721 A | 9/1987 | Ducheyne |
| 4,711,769 A | 12/1987 | Inoue et al. |
| 4,714,721 A | 12/1987 | Franek et al. |
| 4,722,970 A | 2/1988 | Nakagoshi et al. |
| 4,725,234 A | 2/1988 | Ethridge |
| 4,737,411 A | 4/1988 | Graves, Jr. et al. |
| 4,775,646 A | 10/1988 | Hench et al. |
| 4,776,890 A | 10/1988 | Chu |
| 4,780,450 A | 10/1988 | Sauk et al. |
| 4,781,721 A | 11/1988 | Grundei |
| 4,791,939 A | 12/1988 | Maillard |
| 4,795,467 A * | 1/1989 | Piez ........................ A61L 27/46 424/423 |
| 4,803,075 A | 2/1989 | Wallace et al. |
| 4,812,854 A | 3/1989 | Boan et al. |
| 4,849,193 A | 7/1989 | Palmer et al. |
| 4,851,046 A | 7/1989 | Low et al. |
| 4,859,383 A | 8/1989 | Dillon |
| 4,861,733 A | 8/1989 | White |
| 4,868,580 A | 9/1989 | Wade |
| 4,869,906 A | 9/1989 | Dingeldein et al. |
| 4,880,610 A | 11/1989 | Constantz |
| 4,888,366 A | 12/1989 | Chu et al. |
| 4,891,164 A | 1/1990 | Gaffney et al. |
| 4,897,250 A | 1/1990 | Sumita |
| 4,927,866 A | 5/1990 | Purrmann et al. |
| 4,983,573 A | 1/1991 | Bolt et al. |
| 4,988,362 A | 1/1991 | Toriyama et al. |
| 5,011,495 A | 4/1991 | Hollinger |
| 5,034,352 A | 7/1991 | Vit et al. |
| 5,047,031 A | 9/1991 | Constantz |
| 5,053,212 A * | 10/1991 | Constantz ............... A61K 6/033 423/305 |
| 5,108,436 A | 4/1992 | Chu et al. |
| 5,112,354 A | 5/1992 | Sires |
| 5,129,905 A | 7/1992 | Constantz |
| 5,134,009 A | 7/1992 | Ichitsuka et al. |
| 5,204,106 A | 4/1993 | Schepers et al. |
| 5,204,382 A | 4/1993 | Wallace et al. |
| 5,207,710 A | 5/1993 | Chu et al. |
| 5,211,661 A | 5/1993 | Shinjou et al. |
| 5,211,664 A | 5/1993 | Tepic et al. |
| 5,219,829 A | 6/1993 | Bauer et al. |
| 5,221,558 A | 6/1993 | Sonuparlak et al. |
| 5,236,458 A | 8/1993 | Ducheyne et al. |
| 5,236,786 A | 8/1993 | Newkirk et al. |
| 5,238,491 A | 8/1993 | Sugihara et al. |
| 5,256,292 A | 10/1993 | Cagle |
| 5,264,215 A | 11/1993 | Nakabayashi et al. |
| 5,273,964 A | 12/1993 | Lemons |
| 5,276,068 A | 1/1994 | Waknine |
| 5,290,289 A | 3/1994 | Sanders et al. |
| 5,292,678 A | 3/1994 | Dhong et al. |
| 5,296,261 A | 3/1994 | Bouet et al. |
| 5,298,205 A | 3/1994 | Hayes et al. |
| 5,302,362 A | 4/1994 | Bedard |
| 5,306,307 A | 4/1994 | Senter et al. |
| 5,320,844 A | 6/1994 | Liu |
| 5,322,675 A | 6/1994 | Hakamatsuka et al. |
| 5,324,519 A | 6/1994 | Dunn et al. |
| 5,336,642 A | 8/1994 | Wolcott |
| 5,338,334 A | 8/1994 | Zhen et al. |
| 5,338,356 A | 8/1994 | Hirano et al. |
| 5,346,492 A | 9/1994 | Morgan |
| 5,352,715 A | 10/1994 | Wallace et al. |
| 5,409,982 A | 4/1995 | Imura et al. |
| 5,427,754 A | 6/1995 | Nagata et al. |
| 5,435,844 A | 7/1995 | Sasaya |
| 5,464,440 A | 11/1995 | Johansson |
| 5,496,399 A | 3/1996 | Ison et al. |
| 5,503,164 A | 4/1996 | Friedman |
| 5,522,893 A | 6/1996 | Chow et al. |
| 5,525,148 A | 6/1996 | Chow et al. |
| 5,531,794 A | 7/1996 | Takagi et al. |
| 5,545,254 A | 8/1996 | Chow et al. |
| 5,573,537 A | 11/1996 | Rogozinski |
| 5,573,771 A | 11/1996 | Geistlich et al. |
| 5,591,453 A | 1/1997 | Ducheyne et al. |
| 5,626,861 A | 5/1997 | Laurencin et al. |
| 5,645,934 A | 7/1997 | Marcolongo et al. |
| 5,660,778 A | 8/1997 | Ketcham et al. |
| 5,681,872 A | 10/1997 | Erbe |
| 5,702,449 A | 12/1997 | McKay |
| 5,707,962 A | 1/1998 | Chen et al. |
| 5,728,753 A | 3/1998 | Bonfield et al. |
| 5,755,792 A | 5/1998 | Brekke |
| 5,776,193 A | 7/1998 | Kwan et al. |
| 5,824,084 A | 10/1998 | Muschler |
| 5,834,008 A | 11/1998 | Greenspan et al. |
| 5,914,356 A | 6/1999 | Erbe |
| 5,928,243 A | 7/1999 | Guyer |
| 5,939,039 A | 8/1999 | Sapieszko et al. |
| 5,964,809 A | 10/1999 | Lin et al. |
| 5,977,204 A | 11/1999 | Boyan et al. |
| 5,984,968 A | 11/1999 | Park |
| 5,984,969 A | 11/1999 | Matthews et al. |
| 6,017,346 A | 1/2000 | Grotz |
| 6,019,765 A | 2/2000 | Thornhill et al. |
| 6,027,742 A | 2/2000 | Lee et al. |
| 6,049,026 A | 4/2000 | Muschler |
| 6,051,247 A | 4/2000 | Hench et al. |
| 6,077,989 A | 6/2000 | Kandel et al. |
| 6,180,605 B1 | 1/2001 | Chen et al. |
| 6,180,606 B1 | 1/2001 | Chen et al. |
| 6,187,047 B1 | 2/2001 | Kwan et al. |
| 6,190,643 B1 | 2/2001 | Stoor et al. |
| 6,214,368 B1 | 4/2001 | Lee et al. |
| 6,244,871 B1 | 6/2001 | Litkowski et al. |
| 6,287,341 B1 | 9/2001 | Lee et al. |
| 6,288,043 B1 | 9/2001 | Spiro et al. |
| 6,294,187 B1 | 9/2001 | Boyce et al. |
| 6,316,091 B1 | 11/2001 | Richart et al. |
| 6,325,987 B1 | 12/2001 | Sapieszko et al. |
| 6,328,765 B1 | 12/2001 | Hardwick et al. |
| 6,344,496 B1 | 2/2002 | Niederauer et al. |
| 6,383,159 B1 | 5/2002 | Saul et al. |
| 6,383,519 B1 | 5/2002 | Sapieszko et al. |
| 6,428,800 B2 | 8/2002 | Greenspan et al. |
| 6,458,162 B1 | 10/2002 | Koblish et al. |
| 6,482,427 B2 | 11/2002 | Yang |
| 6,521,246 B2 | 2/2003 | Sapieszko et al. |
| D473,648 S | 4/2003 | Muraca |
| 6,582,438 B2 | 6/2003 | DeMayo |
| 6,607,557 B1 | 8/2003 | Brosnahan et al. |
| 6,641,587 B2 | 11/2003 | Scribner et al. |
| 6,652,887 B1 | 11/2003 | Richelsoph et al. |
| 6,696,073 B2 | 2/2004 | Boyce et al. |
| 6,709,744 B1 | 3/2004 | Day et al. |
| 6,723,131 B2 | 4/2004 | Muschler |
| 6,863,899 B2 | 3/2005 | Koblish et al. |
| 6,881,766 B2 | 4/2005 | Hain |
| 6,949,251 B2 | 9/2005 | Dalal et al. |
| 6,969,501 B2 | 11/2005 | Sapieszko et al. |
| 6,987,136 B2 | 1/2006 | Erbe et al. |
| 6,991,803 B2 | 1/2006 | Sapieszko et al. |
| 7,045,125 B2 | 5/2006 | Erbe et al. |
| 7,156,880 B2 | 1/2007 | Evans et al. |
| 7,166,133 B2 | 1/2007 | Evans et al. |
| 7,189,263 B2 | 3/2007 | Erbe et al. |

(56) References Cited

U.S. PATENT DOCUMENTS

| | | | |
|---|---|---|---|
| 7,235,107 | B2 | 6/2007 | Evans et al. |
| 7,241,459 | B2 | 7/2007 | Fechner et al. |
| 7,531,004 | B2 | 5/2009 | Bagga et al. |
| 7,534,451 | B2 | 5/2009 | Erbe et al. |
| 7,931,687 | B2 | 4/2011 | Masuda et al. |
| 2002/0039552 | A1 | 4/2002 | Sapieszko et al. |
| 2002/0062154 | A1 | 5/2002 | Ayers |
| 2002/0127720 | A1* | 9/2002 | Erbe .................. A61L 27/46 435/395 |
| 2003/0055512 | A1 | 3/2003 | Genin et al. |
| 2003/0065400 | A1* | 4/2003 | Beam .................. A61L 27/12 623/23.51 |
| 2003/0138473 | A1 | 7/2003 | Koblish et al. |
| 2003/0180344 | A1 | 9/2003 | Wise et al. |
| 2003/0193104 | A1 | 10/2003 | Melican et al. |
| 2004/0127987 | A1 | 7/2004 | Evans et al. |
| 2004/0138758 | A1 | 7/2004 | Evans et al. |
| 2004/0254538 | A1 | 12/2004 | Murphy et al. |
| 2005/0042288 | A1 | 2/2005 | Koblish et al. |
| 2005/0288795 | A1 | 12/2005 | Bagga et al. |
| 2006/0039951 | A1 | 2/2006 | Sapieszko et al. |
| 2007/0066987 | A1 | 3/2007 | Scanlan et al. |
| 2007/0122447 | A1 | 5/2007 | Koblish et al. |
| 2008/0187571 | A1 | 8/2008 | Clineff et al. |
| 2008/0221701 | A1 | 9/2008 | Zhong et al. |
| 2009/0068285 | A1 | 3/2009 | LeGeros et al. |

FOREIGN PATENT DOCUMENTS

| | | |
|---|---|---|
| JP | 62010939 A | 1/1987 |
| JP | 62067451 A | 3/1987 |
| JP | 62206445 A | 9/1987 |
| JP | 01167209 A | 6/1989 |
| JP | 01249059 | 10/1989 |
| JP | 02149408 A | 6/1990 |
| JP | 04015062 | 1/1992 |
| JP | 04164456 | 6/1992 |
| JP | 04208164 | 7/1992 |
| JP | 09048702 A | 2/1997 |
| JP | 09132406 A | 5/1997 |
| JP | 10243996 | 9/1998 |
| JP | 11106524 | 4/1999 |
| JP | 2001206787 A | 7/2001 |
| WO | 8706843 | 11/1987 |
| WO | 9831630 A1 | 7/1998 |
| WO | 9932163 | 7/1999 |
| WO | 0042991 A1 | 7/2000 |
| WO | 0045871 | 8/2000 |
| WO | 0112106 | 2/2001 |
| WO | 02058755 A2 | 8/2002 |
| WO | 03053290 A1 | 7/2003 |
| WO | 2004030655 A1 | 4/2004 |
| WO | 2005009496 A1 | 2/2005 |
| WO | 2005074614 A2 | 8/2005 |
| WO | 2006031196 A1 | 3/2006 |
| WO | 2007144662 A1 | 12/2007 |
| WO | 2008002682 A2 | 1/2008 |
| WO | 2010146312 A1 | 12/2010 |

OTHER PUBLICATIONS

Ling et al., "Expression of TGF-Beta in Region of Bone Defect Repaired by Collagent/Nano-Beta-Tricalcium Phosphate Composite Artificial Bone," Dabase Medline [online] US National Library of Medicine (NLM), Bethesda, MD, 2003, pp. 302-305, XP002537216, Database Accession No. NLM14526442, Abstract.
Suh et al., "Delivery of Recombinant Human Bone Morphogenetic Protein-2 Using a Compression-Resistant Matrix in Posterolateral Spine Fusion in the Rabbit and in the Non-Human Primate," Database Medline [Online] US National Library of Medicine (NLM), Bethesda, MD, XP002537215, Database Accession No. NLM11840099, Abstract, Feb. 15, 2002, vol. 27, No. 4, pp. 353-360.
Vicente et al., "Ultrastructural Study of the Osteointegration of Bioceramics (Whitlockite and Composite Beta-TCP + Collagen) in Rabbit Bone," Database Medline [Online] US National Library of Medicine (NLM), Bethesda, MD, XP002537217, Database Accession No. NLM8882364, Abstract, Mar.-Apr. 1996, pp. 179-188.
Matsumura et al., "Radiopacity and Physical Properties of Titanium-polymethacrylate Composite," Journal of Dental Research, Jan. 1992, vol. 71, No. 1, pp. 2-6.
U.S. Appl. No. 08/784,439, filed Jan. 16, 1997 Sapieszko et al.
International Search Report for Application No. PCT/US03/31370 dated Dec. 18, 2003.
LeGeros, "Properties of Osteoconductive Biomaterials: Calcium Phosphate", Clinical Orthopaedics and Related Research, Feb. 2002, 395, 81-98.
Pi and Quarles, "A Novel Cation-Sensing Mechanism in Osteoblasts is a Molecular Target", Journal of Bone and Mineral Research, Jan. 12, 2004, 19(5), 862-869.
Vaccaro, "The Role of Osteocondutive Scaffold in Synthetic Bone Graft", Orthopedics, May 2002, 25(5/Supplement), 1-8.
Wong et al. Prediction of precipitation and transformation behavior of calcium phosphate in aqueous media Hydroxyapatite and Related Materials 189-196 1994 CRC Press, Inc.
Vereecke et al. Calculation of the solubility diagrams in the system $Ca(OH)_2\text{-}H_3 \quad PO_4\text{-}KOH\text{-}HNO_3\text{-}CO_2\text{-}H_2 O$ J. Cryst. Growth 1990 104:820.
International Search Report for Application No. PCT/US98/00527 dated Apr. 10, 1998, 1 page.
The Independent Research Group, Jan. 28, 2003, pp. 1-41.
Hench et al., "Biological Applications of Bioactive Glasses," Life Chemistry Reports, 1996, 13, pp. 187-241.
Oonishi et al., "Particulate Bioglass Compared With Hydroxyapatite as a Bone Graft Substitute," Clinical Orthopaedics and Related Research, No. 334, pp. 316-325, 1997.
Abbona et al., "Crystallization of Calcium and Magnesium Phosphates from Solutions of Medium and Low Concentrations," Cryst. Res. Technol., 1992, 27, pp. 41-48.
Brown, "Solubilities of Phosphate and Other Sparingly Soluble Compounds," Environmental Phosphorous Handbook, Chapter 10, 1973, pp. 203-289.
Brown et al., "Variations in Solution Chemistry During the Low-Temperature Formation of Hydroxyapaptite," J. Am. Ceram. Soc., 1991, 74(8), pp. 1845-1854.
Carroll et al., "The Trouble With Tocars; Barely Conscious," Smart Money, 2001.
Cornell et al., "Multicenter Trial of Collagraft as Bone Graft Substitute," J. of Orthopaedic Trauma, 1991, 5(1), pp. 1-8.
Fukase et al., "Setting Reactions and Compressive Strengths of Calcium Phosphate Cements," J. Dent. Res., 1990, 69(12), pp. 1852-1856.
Gosain, "Bioactive Glass for Bone Replacement in Craniomaxillofacial Reconstruction," Bioactive Glass, 2004, 114 (2), pp. 590-593.
Ishikawa et al., "Properties and mechanisms of fast-setting calcium phosphate cements," J. Mat. Sci. Mat. Med., 1995, 6, pp. 528-533.
Koutsoukos et al., "Crystallization of Calcium Phosphates. A Constant Composition Study," J. Am. Chem. Soc., 1980, 102, 1553-1557.
Mirtchi et al., "Calcium phosphate cements: Effect of fluorides on the setting and hardening of b-tricalcium phosphate-dicalcium phosphate-calcite cements," Biomat., 1991, 12, pp. 505-510.
Nancollas, "The involvement of calcium phosphates in biological minerlization and demineralization processes," Pure Appl. Chem., 1992, 64(11), pp. 1673-1678.
Nancollas, "In vitro studies of calcium phosphate crystallization," in Biomineralization Chemical and Biochemical Perspectives, 1989, pp. 157-187.
NovaBone-C/M Synthetic Bone Graft Particulate, POREX Surgical Products Group, 2004, http://www.porexsurgical.com/english/surgical/sprodnova.asp, downloaded from internet on Aug. 22, 2007.
Powell et al., "The Structure of Ceramic Foams Prepared from Polyurethane-Ceramic Suspension," Materials & Manuf. Processes, 1995, 10(4), pp. 757-771.

(56) References Cited

OTHER PUBLICATIONS

Aras et al., "Trace Elements in Human Bone Determined by Neutron Activation Analysis," J. of Radioanalytical and Nuclear Chemistry, 1999, 239(1 ), pp. 79-86.
Bracci et al., "Effect of Mg2+ and Mn2+ on the Chemico-Physical and In Vitro Biological Properties of Calcium Phosphate Biomimetic Coatings," J. of Biochemistry, Sep. 2009, 103, pp. 1666-1674.
Driessens et al., "Effective formulations for the preparation of calcium phosphate bone cements," J. Mat. Sci.: Mat. Med., Mar. 1994, 5(3), pp. 164-170.
Famery et al. "Preparation of alpha-and beta-tricalcium phosphate ceramics, with and without magnesium addition," Caram. Int., Jan. 1994, 20(5), pp. 327-336.
Greenwood et al. "Oxoacids of phosphorus and their salts," in Chemistry of the Elements, Pergamon Press, 1984, pp. 586-595.
Jones, "Teeth and Bones: Applications of Surface Science to Dental Materials and Related Biomaterials," Surface Science Reports, May 2001, 42(3-5), pp. 75-205.
Kingery et al. (eds.), "Introduction to ceramics," 2nd Ed., John Wiley & Sons, 1960, p. 416.
Lacout, "Calcium phosphate as bioceramics," Biomaterials—Hard Tissue Repair and Replacement, Elsevier Science Publishers, 1992, pp. 81-95.
Lee et al., "Tissue-engineered growth of bone by marrow call transplantation using porous calcium metaphosphate matrices," G. Biomed. Mat. Res., Feb. 2001, 54(2), pp. 216-223.
LeGeros "Biodegradation and bioresorption of calcium phosphate ceramics," Clin. Mat., 1993, 14(1 ), pp. 65-88.
LeGeros "Calcium Phosphates in Oral Biology and Medicine," Monographs in Oral Science, Meyers, H.M. (ed.), Karger Press, 1991,15, pp. 108-129.
LeGeros "Preparation of octacalcium phosphate (OCP): A direct fast method," Calcif. Tiss. Int., Mar. 1985, 37, pp. 194-197.
Monma et al., "Properties of hydroxyapatite prepared by the hydrolysis of tricalcium phosphate," J. Chem. Tech. Biotechnol., 1981, 31(1), pp. 15-24.
Nancollas et al., "Formation and dissolution mechanisms of calcium phosphates in aqueous systems," Hydroxyapatite and Related Materials, CRC Press, Inc., 1994, pp. 73-81.
International Patent Application No. PCT/US201 0/061239: International Search Report dated May 2, 2011, 2 pages.
Allan et al., Antibacterial activity of particulate Bioglass against supra- and subgingival bacteria. Biomaterials 2001; 22:1683-1687.
Allan et al., Particulate Bioglass reduces the viability of bacterial biofilms formed on its surface in an in vitro model. Clin Orallmpl Res 2002; 13:53-58.
Stoor P, Soderling E, Salonen JI. Antibacterial effects of a bioactive glass paste on oral microorganisms. Acta Odontol Scand 1998; 56(3):161-165.
Wilson J, Pigott GH, Schoen FJ, Hench L 1. Toxicology and biocompatibility ofbioglasses. J Biomed Mater Res 1981; 15:805-817.
Hench et al., Bonding mechanism at the interface of ceramic prosthetic materials. J. Biomed. Mater. Res. 5:117-141 (1971).
Piotrowski et al., Mechanical studies of the bone bioglass interfacial bond. J. Biomed. Mater. Res. (1975) 9:47-61.
Stanley et al., Residual alveolar ridge maintenance with a new endosseous plant material. Journal of Prostetic Dentistry, vol. 58, pp. 607-613 (1987).
Robson, Wound Infection: a failure of wound healing caused by an imbalance of bacteria. (1997) Surg Clin North Am. pp. 637-650.
U.S. Appl. No. 09/253,556, Sapieszko et al., filed Feb. 19, 1999.
Chaair et al., "Precipitation of stoichiometric apatite tricalcium phosphate prepared by a continuous porcess," J. Mater. Chem., 5(6), pp. 895-899, 1995.
Erbe et al., "Potential of an ultraporous B-tricalcium phosphate synthetic cancellous bone void filler and bone marrow aspirate composite graft", Eur. Spine J., Jun. 13, 2001, 10:S141-S146.
White et al., "Replamineform Porous Biomaterials for Hard Tissue Implant Applications", J. Biomed. Mater. Res. Symposium, 1975, No. 6, 23-27.
Webster's II New College Dictionary; 1995; p. 819.
International Search Report for Application No. PCT/US2007/015424, dated Feb. 16, 2009.
Lickorish, David, et al. Collagen-hydroxyapatite composite prepared by biomimetic process, Journal of Biomedical Materials Research Part A. vol. 68A (Nov. 14, 2003), pp. 19-27.
European Search Report and European Opinion for Application No. EP12151422 dated Jun. 11, 2012.
Database WPI Week 200172, Thomson Scientific, London, GB; AN 2001-620274, XP002676997, Jul. 31, 2001.
Database EPODOC, European Patent Office, The Hague, NL; XP002676998, Jul. 31, 2001.
Australian Search Report for Application No. 2007265379 dated Dec. 24, 2012.
Australian Search Report for Application No. 2007265379 dated Jan. 7, 2013.
Canadian Office Action for Application No. 2656050 dated Jul. 22, 2013.
Yao et al., "The effect of bioactive glass content on synthesis and bioactivity of composite poly (lactic-co-glycolic acid)/bioactive glass substrate for tissue engineering", Biomaterials, vol. 26., pp. 1935-1943, 2005.
Japanese Office Action for Application No. 2009-518354 dated Jul. 12, 2013.
Australian Examination Report for Application No. 2012244219 dated Sep. 6, 2013.
Australian Examination Report for Application No. 2007265379 dated Sep. 16, 2013.
Etherington, D.J., "Collagen Degradation", vol. 36, Jan. 1, 1977, pp. 14-17, XP55015927, Retrieved from the Internet: <http://ard.bmj.com/content/36/Suppl_2/14.full.pdf> [retrieved on Jan. 9, 2012].
European Search Report for EP Application No. 16175575.6 dated Sep. 15, 2016.

* cited by examiner

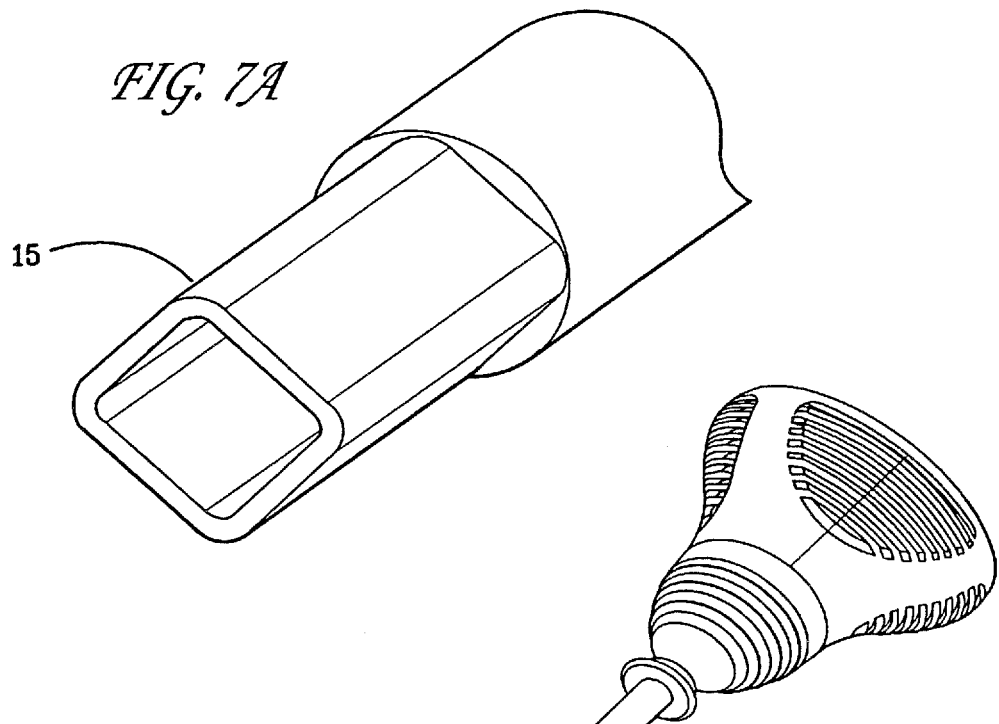
FIG. 7A
FIG. 7B
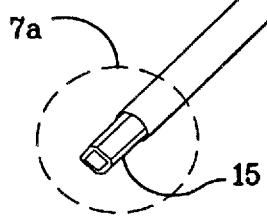

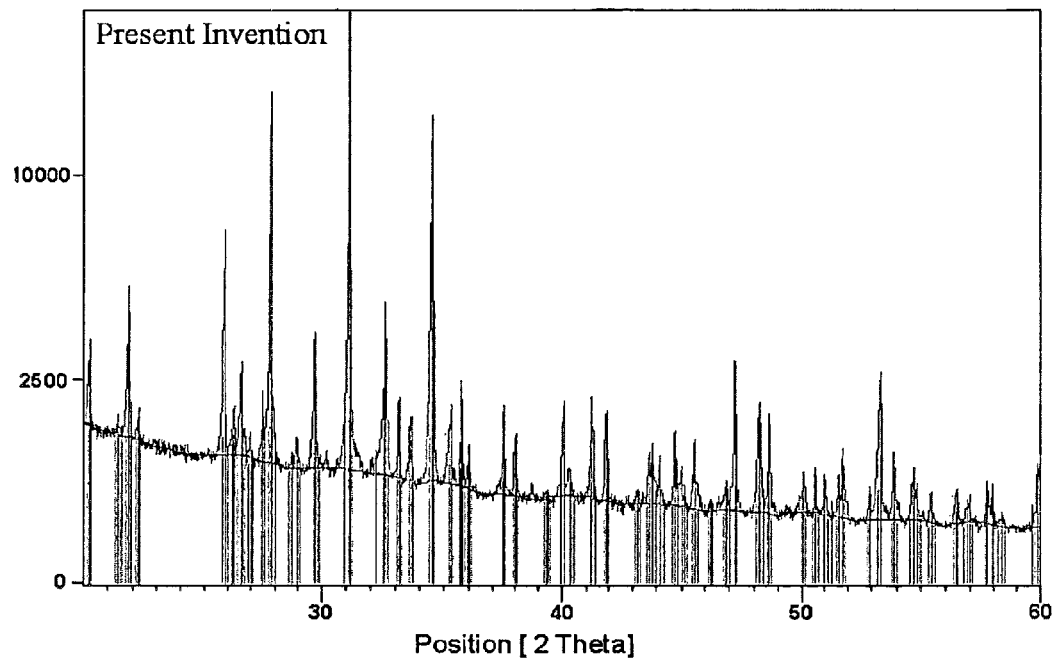
Figure 9. Representative XRD spectra of embodiment of present invention (top) vs. β-TCP (bottom)
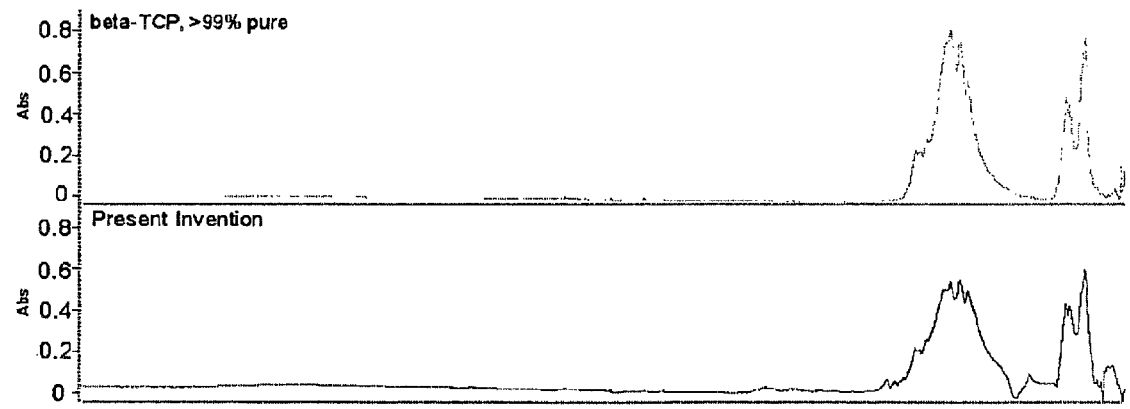
Figure 10. Representative FTIR spectrum of embodiment of present invention vs. β-TCP (beta-TCP)

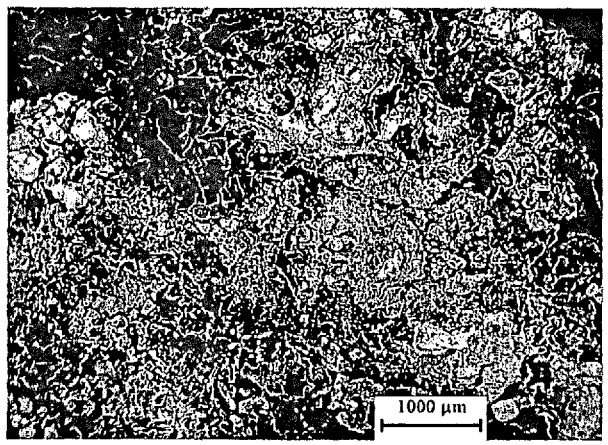
Figure 11. SEM, 20x
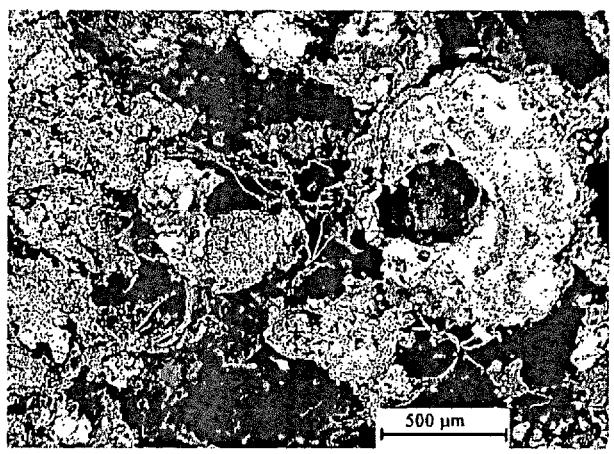
Figure 12. SEM, 50x
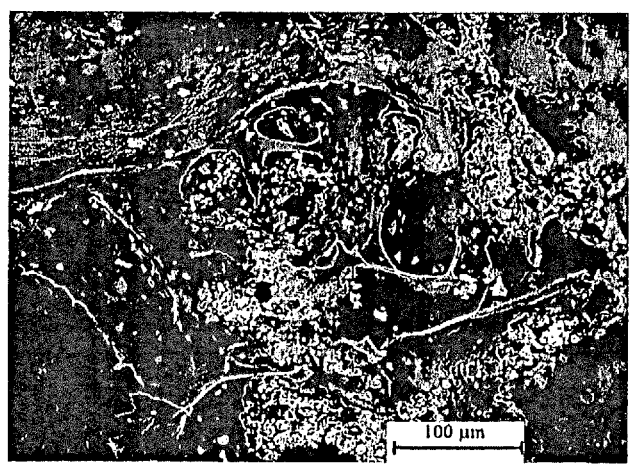
Figure 13. SEM, 250x

SHAPEABLE BONE GRAFT SUBSTITUTE AND INSTRUMENTS FOR DELIVERY THEREOF

CROSS REFERENCE TO RELATED APPLICATIONS

The present application is a divisional of U.S patent application Ser. No. 10/874,994, filed on Jun. 23, 2004, the disclosure of which is incorporated herein by reference.

FIELD OF THE INVENTION

This invention relates to porous, shapeable biocompatible bone graft materials for repairing bone defects, the application of the bone graft materials disclosed herein and tools for delivering the bone graft materials. The present invention bone graft materials incorporate the benefits of porous inorganic shaped bodies having macro, meso, and microporosity and polymers such as collagen. The present invention is particularly suitable as an injectable for filling bone defects of various shapes and sizes.

BACKGROUND OF THE INVENTION

The use of natural and synthetic materials for bone repair is known. Most of the synthetic materials share numerous advantages over natural materials (including allograft bone, autograft bone and demineralized bone matrix ("DBM")) such as unlimited supply, elimination of disease transmission, elimination of second surgery, and the ability to be shaped into various shapes and sizes. Many synthetic bone grafts include materials that closely mimic mammalian bone, such as compositions containing calcium phosphates. Exemplary calcium phosphate compositions contain type-B carbonated hydroxyapatite $[Ca_5(PO_4)_{3x}(CO_3)_x(OH)]$, which is the principal mineral phase found in the mammalian body. The ultimate composition, crystal size, morphology, and structure of the body portions formed from the hydroxyapatite are determined by variations in the protein and organic content. Calcium phosphate ceramics have been fabricated and implanted in mammals in various forms including, but not limited to, shaped bodies and cements. Different stoichiometric compositions such as hydroxyapatite ("HAp"), tricalcium phosphate ("TCP"), tetracalcium phosphate ("TTCP"), and other calcium phosphate salts and minerals, have all been employed to match the adaptability, biocompatibility, structure, and strength of natural bone. The role of pore size and porosity in promoting revascularization, healing, and remodeling of bone has been recognized as a critical property for bone grafting materials. The preparation of exemplary porous calcium phosphate materials that closely resemble bone have been disclosed, for instance, in U.S. Pat. Nos. 6,383,519 and 6,521,246, incorporated herein by reference in their entirety.

Recently, in an attempt to broaden the use of bone graft materials throughout the body, pliable and injectable bone graft compositions have been fabricated. Some of these attempts have been disclosed in U.S. Pat. No. 5,324,519 to Dunn, et al.; U.S. Pat. No. 5,352,715 to Wallace et al.; U.S. Pat. No. 6,287,341 to Lee et al.; U.S. Pat. No. 6,214,368 to Lee et al.; U.S. Pat. No. 6,652,887 to Richelsoph et al.; and U.S. Pat. No. 6,288,043 to Spiro et al. However, these attempts suffer from numerous shortcomings. Some compositions are made of thermoplastic polymers as opposed to calcium phosphate. There are injectable implant compositions that teach having ceramic:collagen ratios requiring a collagen dominance. There are also compositions used as implants made of poorly crystalline apatitic calcium phosphate defined by a specific XRD spectrum and FTIR pattern. Other attempts have focused on compositions made from calcium sulfate.

Furthermore, many of these bone attempts include materials that do not optimally resorb (e.g., thermoplastic polymers, amorphous calcium phosphate, calcium sulfate dihydrate) or structures that do not have the ideal porosity and pore size distribution to promote bone formation. Other attempts require the addition of a carrier, such as hyaluronic acid or glycerol, or a plasticizer in a high percentage so that the compositions may be shaped or injected. Several also require that the mineral component particle size be smaller than 250 µm to facilitate injection.

There is a need for resorbable, porous, shapeable bone graft materials that maintain ideal osteoconductivity properties and offer convenient delivery for a variety of applications. The present invention includes optimal materials, with optimal porosities in optimal size ranges for promoting bone formation. Although generally useful, the present invention is particularly suitable in trauma and orthopaedic applications, in which the size and the shape of the defects to be repaired are irregular or variable.

It is an object of this invention to provide biocompatible graft materials with superior osteoconductive properties.

It is also an object of this invention to provide flowable graft materials for restoring defects in bone.

It is another object of this invention to provide shapeable bone graft materials that can occupy voids of varying shapes.

It is another object of this invention to provide injectable bone graft materials with improved handling properties that resorb.

It is yet another object of this invention to provide injectable bone graft materials that still retain high degrees of porosity over a broad pore size distribution to maintain superior resorption and bone ingrowth properties.

It is yet another object of the invention to provide injectable bone graft materials with fluid wicking and retention properties.

It is also an object of this invention to provide porous, pliable bone graft materials capable of delivering cells and molecules to the body.

It is also an object of this invention to provide a bone graft material capable of being mixed with other graft materials while maintaining injectability.

It is a further object of this invention to provide an injectable, resorbable bone graft material and instruments for delivery thereof.

It is a further object of this invention to provide bone grafts with delivery instruments capable of low-pressure delivery of injectable bone graft materials.

Additional objects, advantages, and novel features of this invention will become apparent to those skilled in the art upon examination of the following descriptions, figures and claims thereof, which are not intended to be limiting.

SUMMARY OF THE INVENTION

An embodiment of the present invention is directed to a flowable body comprising from about 15% to about 30% by weight of biocompatible polymer, an inorganic composition comprising calcium phosphate with a size range of about 100 µm to about 4000 µm and all combinations and subcombinations therein, said flowable body being imbibed with a fluid. Another embodiment is directed to a flowable body having macro-, meso-, and microporosity comprising from about 15% to about 30% by weight of biocompatible polymer and all combinations and subcombinations therein, a material with a size range of about 100 μm to about 4000 μm and all combinations and subcombinations therein, comprising the oxidation-reduction reaction product of at least one metal cation, at least one oxidizing agent, and at least one oxidizable precursor anion, and said flowable body being imbibed with a fluid. Suitable polymers may include organic materials such as collagen, soluble collagen, or soluble collagen limited to cross-links. The reaction product may be selected to suit the needs of one skilled in the art but may be inorganic compositions comprising calcium phosphate, biphasic calcium phosphate, or beta tri-calcium phosphate (β-TCP). The present invention is also directed to instruments for delivering the bone graft materials to various parts of the body.

It has been discovered that admixing highly porous resorbable inorganic bodies with certain resorbable polymeric materials greatly improves handling, yet still provides an osteoconductive implant with good resorption and bone formation properties. The materials can be easily shaped after contact with a biological fluid with minimal mixing and can be delivered via injection through delivery tubes of varying diameters while maintaining optimal porosity and pore size distribution for resorption, cellular infiltration and imbibation. These implants offer easy-to-use doses of composite material and are a significant advancement over current bone graft systems for clinical applications.

The present invention is an improvement upon the shaped bodies disclosed in U.S. Pat. No. 6,383,519 ("'519 patent") and U.S. Pat. No. 6,521,246 ("'246 patent"), and the RPR process disclosed in U.S. Pat. No. 5,939,039 ("'039 patent") and U.S. Pat. No. 6,325,987 ("'987 patent"), all assigned to the present assignee and incorporated herein by reference in their entirety. The oxidation-reduction reaction product exemplified in the present invention shares the same unique porosity of those shaped bodies of the '519 and '246 patents. The reaction product confers upon the graft materials of the present invention macro, meso, and microporosity, which allow the graft material to have extraordinary imbibation and absorption properties. Further, the inclusion of the specific polymers in the present invention material lends improved handling and injectability. The graft materials can have a finite shape when dry and can be wetted prior to use to produce a putty-like mass that can be injected into the site. In this manner, the bone graft can be stored dry so as to not compromise shelf-life. For use, the dry shape, whether it be a cylinder, block, strip, sheet, wedge or otherwise is wetted preferably with a pre-determined amount of fluid. Fluids such as bone marrow aspirate, blood, or saline are useful in embodiments of the present injectable bone graft material; however, other biocompatible/biological fluids may be used. The present invention can be injected using standard off-the-shelf syringes or, preferably, can be delivered using the novel delivery tools described herein.

Some embodiments of this invention give rise to biocompatible, resorbable composites that have from about 15% to about 30% by weight of the biocompatible polymer and all combinations and subcombinations therein and from about 70% to about 95% by weight of the reaction product. The amount of biocompatible polymer within the bone graft materials may be from about 15% to about 20% by weight, or alternatively, 15% to about 25% by weight. In some embodiments that may be preferred, the size of the mineral component may be between about 250 μm and about 4000 μm and all combinations and subcombinations therein. This allows the bone graft material to be delivered through small orifices, yet maintains enough porosity to allow capillary action, cellular infiltration, and vascular incorporation.

The present invention finds particular suitability in applications that require irregularly shaped and sized bone void defects to be filled.

DESCRIPTION OF THE DRAWINGS

FIGS. 7A and 7B illustrate an embodiment of the delivery system tube 10 in which the end of the tube has a flow adapter 15 for directing the delivery.

FIG. 9 is a representative XRD spectra of a bone graft material of the present invention (top) vs. β-TCP standard (bottom).

FIG. 10 is a representative FTIR spectrum of bone graft material of the present invention vs. β-TCP.

FIG. 11 is an SEM of the bone graft material, 20×.
FIG. 12 is an SEM of the bone graft material, 50×.
FIG. 13 is an SEM of the bone graft material, 250×.

DETAILED DESCRIPTION OF PREFERRED EMBODIMENTS

Figure 1A:
FIG. 1A illustrates one basic dry form of the biocompatible graft material in cylindrical shaper.

In accordance with the present invention, flowable graft materials are provided comprising from about 15% to about 30% by weight of biocompatible polymer and all combinations and subcombinations therein, an inorganic composition comprising calcium phosphate with a size range of about 100 μm to about 4000 μm and all combinations and subcombinations therein, and said flowable body being imbibed with a fluid. Graft materials are also provided that comprise a collagen and macro-, meso-, and microporous calcium phosphate. As used herein, a "flowable body" is a body that can be induced to flow like a viscous liquid while maintaining coherency or, alternatively, is a body that can be injected through a tubular structure while maintaining coherency.

Some embodiments may comprise up to 100% Type I collagen. In other embodiments, the collagens used may be up to about 90% of Type I collagen with up to about 5% of Type III collagen and a small percentage of other types. The Type I bovine collagen may be native fibrous insoluble collagen, soluble collagen, reconstituted collagen, or combinations thereof. In a preferred embodiment, the collagen used is predominantly soluble Type I collagen. The biocompatible polymer may be combined with the reaction product in slurry form, or combined by blending or kneading, to form a substantially homogenous mixture. As used in this context, substantially homogenous means that the ratio of components within the mixture is the same throughout. This, upon treatment using various preferred freeze-drying, heating and processing techniques, produces a form of the present invention graft material that may be preferred. Upon wetting the form with a pre-determined amount of fluid, the material becomes a pliable mass that can be delivered to the site or injected into the site using standard or custom delivery instruments as described herein.

Collagen has been found to be particularly suitable in the present invention for use as a biocompatible polymer. The admixture of the collagen with the highly porous reaction product results in a graft that is highly porous with a broad pore size distribution, increased handling properties, and pliability beyond that which can be achieved with some forms of the reaction product alone—for instance calcium phosphate. The resorption profile of some of the embodiments of the present invention may vary depending upon the amount, nature, and source of the collagen or other polymer used. Typically, by twelve weeks in vivo an effective amount of the present invention is resorbed. One reason that may explain the superior resorption properties of the present invention is the high degree of porosity retained even upon admixing the collagen with the reaction product. The collagen may be a soluble collagen with limited cross-links.

Preferable collagens have biochemical attributes such as about 10% to about 20% nitrogen content, about 10% to about 15% of hydroxyproline, or up to about 2.5% of ash content. In some embodiments, the collagens may be about 10.5% to about 17% nitrogen, about 10.5% to about 14% of hydroxyproline, or up to about 2.5% of ash content. The percent nitrogen of a collagen is a measurement of nitrogen in a sample. In the presence of sulfuric acid, the amino nitrogen of organic material is converted to ammonium sulfate. The ammonium sulfate is distilled from an alkaline medium, and further decomposes from which the ammonia is absorbed into a boric acid solution containing a pH indicator. The ammonia (nitrogen) concentration may be determined colorimetrically by back titrating the boric acid solution with a standard acid.

The percent hydroxyproline of a collagen is a measure of hydroxyproline in a sample. Collagen is hydrolyzed with dilute Hydrochloric Acid, filtered and diluted. The solution is reacted with several reagents and then measured using ultraviolet (UV)/Vis analysis along with a standard hydroxyproline solution. Using the sample and standard absorbances, the percentage of hydroxyproline can be calculated [(Sample Abs)(Std)(Weight)(dilution factor)]/[(Sample weight)(Std. Abs)(dilution factor)].

The ash content of collagen is a measure of the amount of residual elements in collagen materials. When collagen is heated to extremely high temperatures, it is converted to mainly carbon dioxide and water. Elements other than collagen and hydrogen are converted to oxides and salts. A small sample of material is heated until there is only ash left. The weight of this ash is considered the gross amount of inorganic/organic material of the original sample.

Bone graft materials of this invention that may be preferred are held together in surgically relevant shapes and sizes by forming the inorganic reaction product with the collagen. The resulting articles retain substantially all of the biological and chemical properties of the shaped bodies taught in the '519 and '246 patents, while forming a unit dose, which upon wetting, become pliable, shapeable or injectable.

Figure 1B:
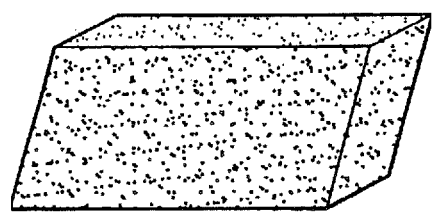
FIGS. 1B and 1C illustrate other exemplary shapes the grafts may take.
Figure 1C:
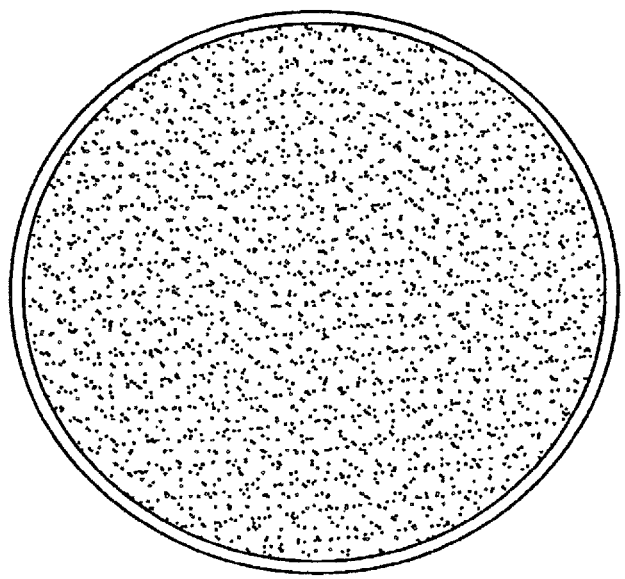
Figure 1D:
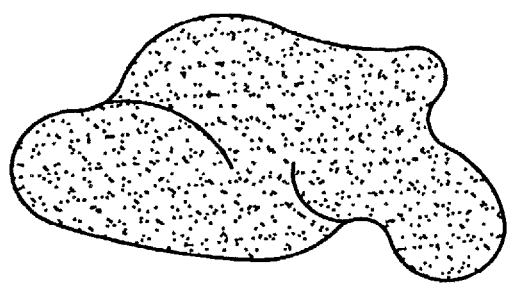
FIG. 1D illustrates that the graft may be shapeable after being wetted with fluid such as saline, blood, bone marrow aspirate or other such biological material.

The bone graft materials may be manufactured into various shapes of prescribed dimensions and volumes. As shown in FIG. 1A, the material may take the form of a cylinder. Upon being wetted (FIG. 1B), the material reduces to a pliable mass, which can be delivered to or injected into the site. Following delivery in the surgical site, the graft material will resorb and exhibit the same beneficial biological responses (e.g., bone formation) as the aforementioned shaped bodies.

Figure 2A:
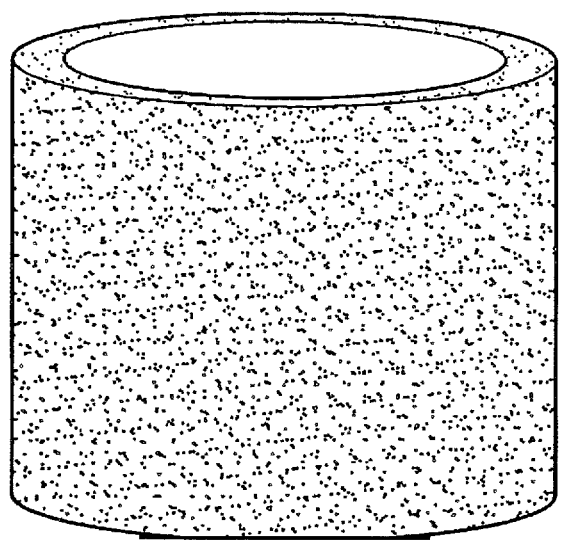
FIGS. 2A and 2B illustrate other forms of the biocompatible graft material in cup form with an internal cavity sized to receive a precise amount of fluid.
Figure 2B:
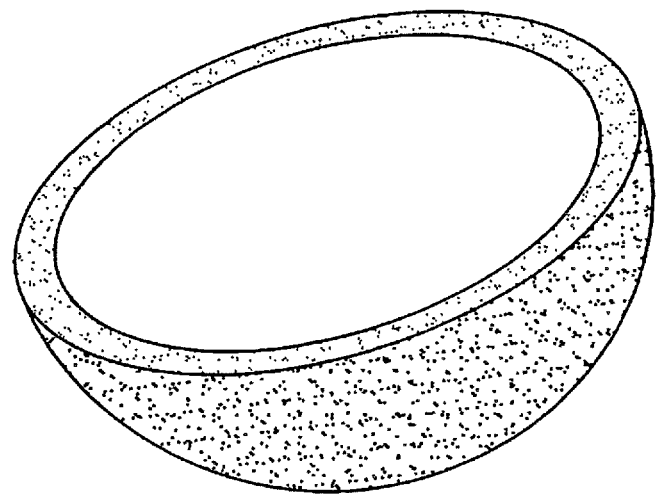

FIG. 2 is an alternate embodiment of the present invention in which the bone graft material takes the shape of a cup with an internal cavity sized to receive the optimal amount of fluid for forming the bone graft into a pliable mass. This embodiment eliminates the need for the user to determine and measure the amount of fluid to add to the bone graft.

In some embodiments, the bone graft materials may have from about 15% to about 30% by weight of biocompatible polymer and all combinations and subcombinations therein. The biocompatible polymer may also be from about 15% to about 20% by weight in other embodiments. It will be appreciated that embodiments exist wherein the bone graft materials have from about 15% to about 20% or from about 20% to about 30%. In other embodiments where the polymer chosen is a collagen, the present invention exhibits a unique mineral (e.g., β-TCP, TCP, TTCP, HAp, HAp/TCP combo) to collagen ratio that is unlike the ratios shared by other bone grafts. However, one skilled in the art may obtain bone graft materials of variable ratios depending on their particular needs. In one effective embodiment, the mass ratio of the reaction product and the collagen is 80:20. In others, it may be 90:10 or 70:30. The mass ratio may be altered without unreasonable testing using methods readily available in the art. It will be appreciated that this ratio is contrary to the mineral β-TCP to collagen ratios one skilled in the art would find in previous bone grafts while still maintaining all the properties (e.g., porosity, pore size distribution) that attribute to an effective bone graft (e.g., simultaneous bone formation, strength and graft resorption). The bone graft is also capable of maintaining injectability at this ratio without separation of the fluid from the inorganic or collagen component or separation of the inorganic and collagen components from each other.

It appears that due to the high porosity and broad pore size distribution of many embodiments of the present invention, the graft is not only able to wick, soak, and imbibe materials very quickly, but is also capable of retaining them. A variety of fluids could be used with the present invention including blood, bone marrow aspirate, saline, antibiotics, proteins such as bone morphogenetic proteins ("BMP"), molecules, vectors, therapeutic agents, and combinations thereof. Unlike other injectable bone graft materials, some embodiments of the present invention do not require materials such as glycerol, hyaluronic acid, or the like, to serve as the carrier for the mineral phosphate; rather, biological fluid or saline is the carrier for the present invention. After mixing with biological fluids such as blood, bone marrow aspirate, or saline, the present invention is capable of being delivered via injection through small orifices such as 17-gauge cannulas or catheters.

Materials of the present invention can also be imbibed with cells (e.g. bone cells such as osteoblasts and osteocytes, fibroblasts, and cells such as mesenchymal, stromal, marrow and stem cells), protein rich plasma, other biological fluids and any combination of the above. This capability has utility in cell-seeding, drug delivery, and delivery of biologic molecules as well as in the application of bone tissue engineering, orthopaedics, and carriers of pharmaceuticals. The cells may be seeded onto the graft prior to implantation. Similarly, molecules or proteins could be soaked into the graft prior to implantation.

Bone graft materials of the present invention that may be preferred exhibit high degrees of porosity. It is also preferred that the porosity occur in a broad range of effective pore sizes. In this regard, persons skilled in the art will appreciate that preferred embodiments of the invention may have, at once, macroporosity, mesoporosity, and microporosity. Macroporosity is characterized by pore diameters greater than about 100 µm and, in some embodiments, up to about 1000 µm to 2000 µm. Mesoporosity is characterized by pore diameters between about 100 µm and 10 µm, while microporosity occurs when pores have diameters below about 10 µm. It is preferred that macro-, meso-, and microporosity occur simultaneously and are interconnected in products of the invention. It is not necessary to quantify each type of porosity to a high degree. Rather, persons skilled in the art can easily determine whether a material has each type of porosity through examination, such as through the preferred methods of mercury intrusion porosimetry, helium pycnometry and scanning electron microscopy. While it is certainly true that more than one or a few pores within the requisite size range are needed in order to characterize a sample as having a substantial degree of that particular form of porosity, no specific number or percentage is called for. Rather, a qualitative evaluation by persons skilled in the art shall be used to determine macro-, meso-, and microporosity.

It will be appreciated that in some embodiments of materials prepared in accordance with this invention, the overall porosity will be high. This characteristic is measured by pore volume, expressed as a percentage. Zero percent pore volume refers to a fully dense material, which, in essence, has no pores at all. One hundred percent pore volume cannot meaningfully exist since it would refer to "all pores" or air. Persons skilled in the art understand the concept of pore volume, however, and can easily calculate and apply it. For example, pore volume may be determined in accordance with Kingery, W. D., *Introduction to Ceramics*, Wiley Series on the Science and Technology of Materials, $1^{st}$ Ed., Hollowman, J. H., et al. (Eds.), Wiley & Sons, 1960, p. 409-417, who provides a formula for determination of porosity. Expressing porosity as a percentage yields pore volume. The formula is: Pore Volume=$(1-f_p)$ 100%, where $f_p$ is fraction of theoretical density achieved.

Porosity can be measured by Helium Pycnometry. This procedure determines the density and true volume of a sample by measuring the pressure change of helium in a calibrated volume. A sample of known weight and dimensions is placed in the pycnometer, which determines density and volume. From the sample's mass, the pycnometer determines true density and volume. From measured dimensions, apparent density and volume can be determined. Porosity of the sample is then calculated using (apparent volume−measured volume)/apparent volume. Porosity and pore size distribution may also be measured by mercury intrusion porosimetry.

Pore volumes in excess of about 30% may be achieved in accordance with this invention while materials having pore volumes in excess of about 50% or about 60% may also be routinely attainable. Some embodiments of the invention may have pore volumes of at least about 70%. Some embodiments that may be preferred have pore volumes in excess of about 80%, with about 85% being still more preferred. Pore volumes greater than about 90% are possible as are volumes greater than about 92%. In some preferred cases, such high pore volumes are attained while also attaining the presence of macro-, meso-, and microporosity as well as physical stability of the materials produced.

Figure 3:
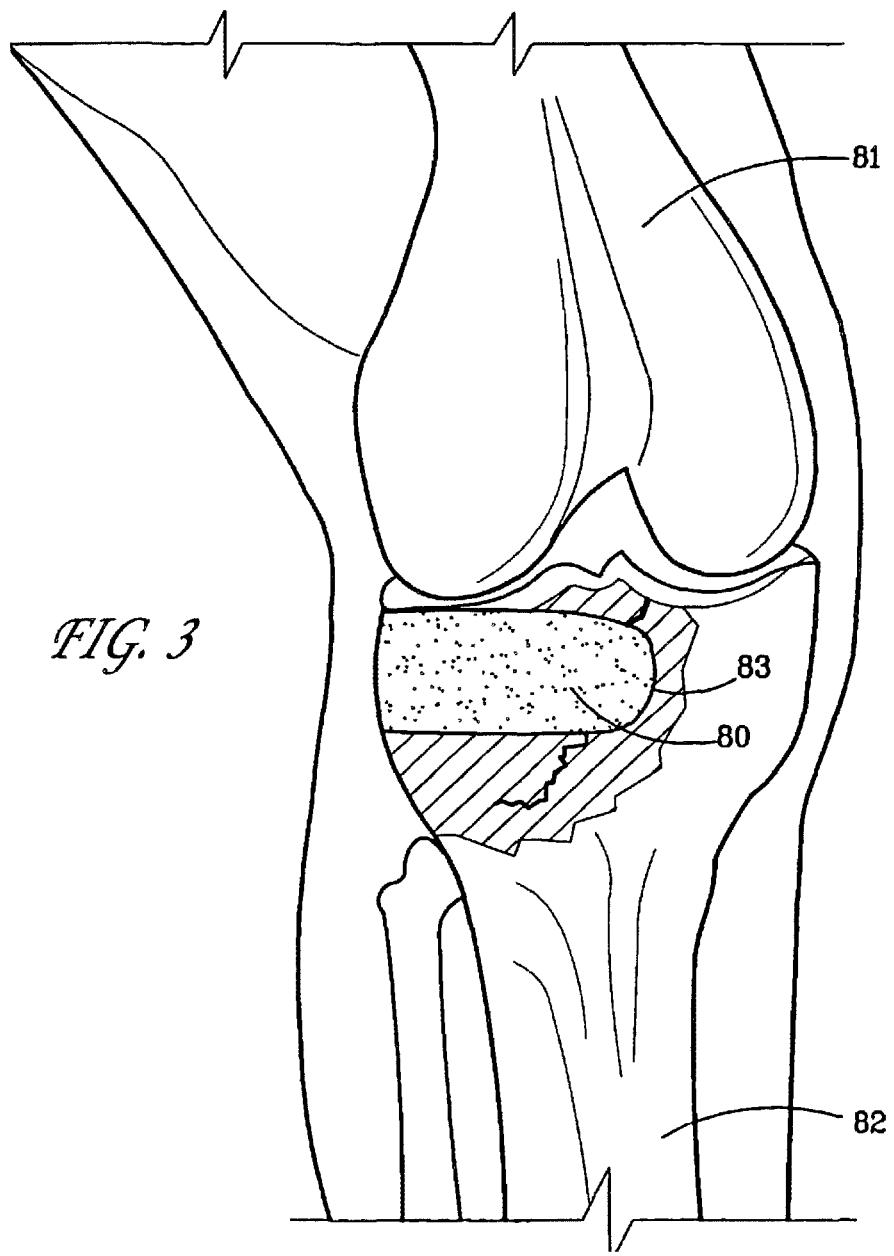
FIG. 3 depicts the graft material 80 injected into a bone void 83 below the femur 81 in the tibial plateau 82 within a human knee.
Figure 4:
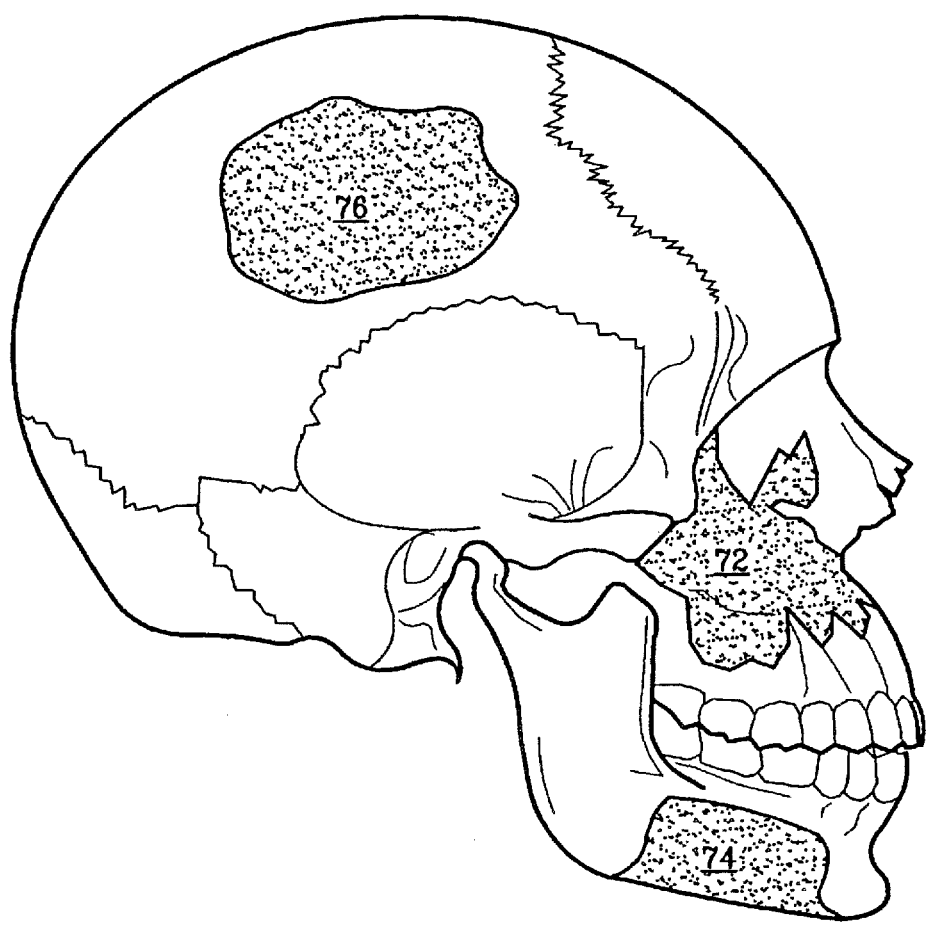
FIG. 4 illustrates the graft material of the present invention injected to serve as a cranio-maxillofacial 76, zygomatic reconstruction 72, and mandibular implant 74.
Figure 5:
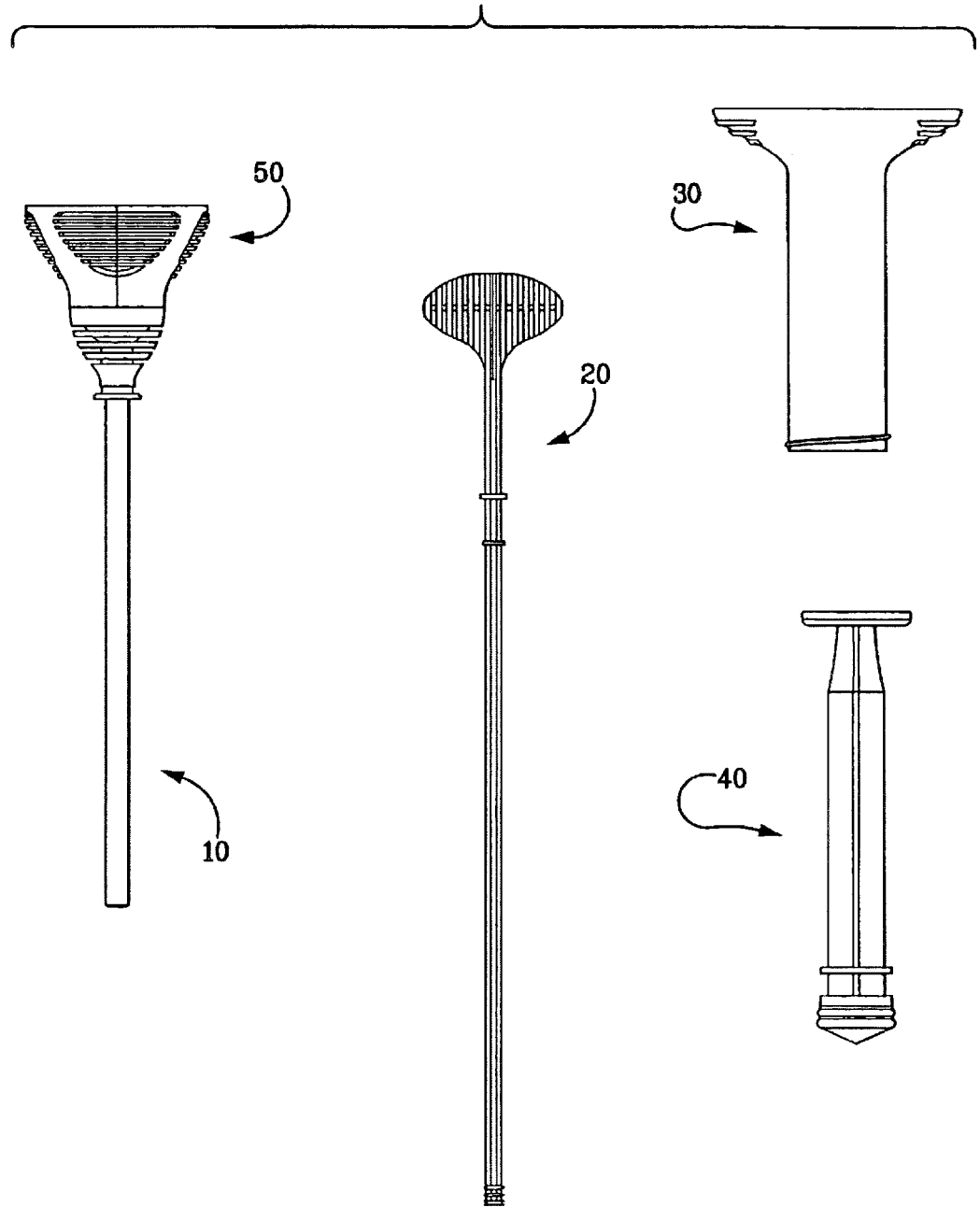
FIG. 5 illustrates one embodiment of the delivery system components of the present invention including a delivery tube 10, plunger 20, a syringe body 30, and piston 40.
Figure 6:
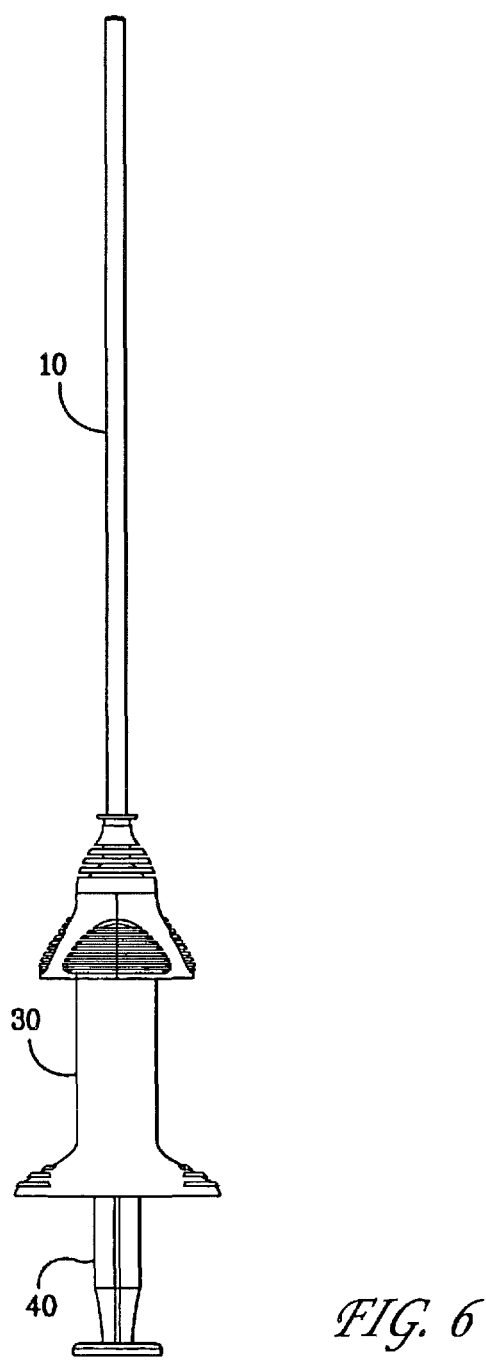
FIG. 6 illustrates the delivery tube 10, the syringe body 30, and piston 40 assembled in the delivery system.

Due to this porosity, the bone graft materials disclosed herein may soak fluids rapidly. Fluids that may be used in the present invention include bone marrow aspirate, blood, saline, antibiotics and proteins such as BMP and the like. Once wetted, soaked or mixed with fluid, the bone graft becomes a putty-like mass with a reduction in volume. The material may then be placed in a bone void such as those shown in FIGS. 3 and 4. The bone graft may be placed by hand or can be injected or inserted using an appropriate delivery device. An exemplary, although not exclusive, embodiment is depicted in FIGS. 5-7B.

As shown, once the bone graft material of FIG. 1A is wetted with fluid, it can be kneaded to form a putty-like mass. If desired, the present invention can be mixed with other available bone graft materials including autograft and allograft bone chips, DBM and synthetic morsels that are within the size range of about 250 µm to about 4000 µm and all combinations and subcombinations therein. After mixing, the mass can be transferred to and packed into the syringe body 30. The delivery tube 10 may then be threaded to the front of the syringe body 30. Preferably, the delivery tube 10 is then positioned to the delivery site and the syringe piston 40 is then completely depressed to deliver the bone graft material to the site. Any residual material in the delivery tube 10 can be expelled via the plunger 20. Alternatively, after the delivery tube 10 is threaded to the syringe body 30 and the bone graft material advances into the delivery tube 10 from the syringe body 30 by depression of the syringe piston 40, the syringe piston 40 can be released and the syringe body 30 can be removed from the delivery tube 10. The delivery tube 10 with the bone graft material inside can then be positioned to the desired surgical site and the plunger 20 can be advanced into the delivery tube 10 to deliver the bone graft material. The delivery tube 10 and plunger 20 can be made of various plastics or metals, but preferably have a radiopacity that distinguishes them from the bone graft material and allows them to be visualized under fluoroscopy. In this manner, the tube, the bone graft material inside the tube and the anatomical structures are all radiographically distinguishable. Materials such as polypropylene, polyethylene, polycarbonate, polyurethane, nylon, polyolefins and other engineering plastics are preferred for the tube and plunger. Additionally, these materials may include fillers for radiopacity including barium sulfate, bismuth subcarbonate and bismuth trioxide.

The length of the delivery tube 10 should be such to allow delivery in situations requiring longer lengths. Delivery tubes that may be used in conjunction with the present invention may preferably be from about 5 inches to about 12 inches in length or from about 6 inches to about 10 inches in length. The tubes may preferably house about 10 cc to about 20 cc of material. The tubing may be rigid or flexible to suit the application. In a preferred embodiment, the tubing is flexible to allow manipulation around anatomical constraints during the procedure. Features of the delivery system comprise an integral funnel hub 50 attached to end of the delivery tube 10 to allow ergonomic delivery and to prevent inadvertent spillage of bone graft material during the loading and delivery stages. The funnel hub 50 also includes threads on the inside for mating with the threads on the end of the syringe body. The assembly of the delivery components of the present invention ensures stability of the construct for manipulation prior to and during delivery via the shape of grips of the funnel hub 50, and prevents spillage of valuable bone graft material. Further, the assembly of the delivery components of the present invention allows for low force injection. That is, the extrusion force required to deliver the material via the syringe body through the tube is less than 50 lbs, and preferably less than 25 lbs. in some embodiments the extrusion force is between about 20 lbs to about 25 lbs. Optionally, the delivery tube of the present invention may be provided with a flow adapter at one end (FIGS. 7A & 7B). The flow adapter can be shaped to mate with various openings of a load-bearing implant to aid in the delivery of the material to fill all the open cavities.

In use for repairing bone voids, the user wets the bone graft material with a predetermined amount of fluid. In a preferred embodiment, the ratio for wetting the bone graft to obtain the desired mass with an appropriate viscosity for injecting and repairing bone voids is 2.0 cc-2.5 cc fluid per 5 cc of dry bone graft material. Wetting can either be performed by immersing the dry bone graft material in the fluid or squirting the fluid onto the bone graft material. The wetted bone graft material can be placed aside to let the fluid diffuse into the material before kneading or can be kneaded immediately. The kneaded mass can then be placed into the surgical site by hand, via standard surgical tools or delivery devices, or preferably using the delivery components of the present invention.

In one embodiment of the present invention, the bone graft material is provided inside a cartridge and the fluid is injected or aspirated directly into the cartridge. Upon application of positive pressure for a period of time, the fluid mixes with the bone graft material to provide a pliable, homogeneous mass that can be injected into the site without requiring the user to touch or knead the material.

In another embodiment of the present invention, the surface area and porosity of the bone graft material is increased by making channels parallel to the longitudinal axis of the cylinder. The cylindrical bone graft material is then placed inside the barrel of a cartridge. Upon injection or aspiration of fluid into the cartridge (without application of a positive pressure), the fluid mixes with the bone graft material to provide a pliable, homogeneous mass that can be injected.

In accordance with the present invention, some bone graft materials disclosed may be partially comprised of materials, morsels, or particles resulting from an oxidation-reduction reaction. These materials may be produced by methods comprising preparing an aqueous solution of a metal cation and at least one oxidizing agent. The solution is augmented with at least one soluble precursor anion oxidizable by said oxidizing agent to give rise to the precipitant oxoanion. The oxidation-reduction reaction thus contemplated is conveniently initiated by heating the solution under conditions of temperature and pressure effective to give rise to said reaction. In accordance with preferred embodiments of the invention, the oxidation-reduction reaction causes at least one gaseous product to evolve and the desired intermediate precursor mineral to precipitate from the solution.

The intermediate precursor mineral thus prepared can either be used "as is" or can be treated in a number of ways. Thus, it may be heat-treated to a temperature greater than about 800° C. or greater than about 1100° C. in accordance with one or more embodiments to provide a preselected crystal structure or other preselected morphological structures therein. In accordance with preferred embodiments, the oxidizing agent is nitrate ion and the gaseous product is a nitrogen oxide, generically depicted as $NO_{x(g)}$. It may be preferred that the precursor mineral provided by some embodiments be substantially homogenous. As used in this context, substantially homogenous means that the porosity and pore size distribution throughout the precursor mineral is the same throughout.

In accordance with other preferred embodiments, the intermediate precursor mineral provided by the present invention may be any calcium salt. Subsequent modest heat treatments convert the intermediate material to, for example, novel monophasic calcium phosphate minerals or novel biphasic β-tricalcium phosphate (β-TCP)+type-B, carbonated apatite (c-HAp) $[\beta-Ca_3(PO_4)_2+Ca_5(PO_4)_{3-x}(CO_3)_x(OH)]$ particulates. More preferably, the heat treatment converts the intermediate material to a predominantly β-TCP material. The size of the mineral component that can be used in the present invention may vary depending upon the application and orifice size of the delivery instrument. Preferably the mineral component comprises morsels having a size ranging from about 100 μm to about 4000 μm and all combinations and subcombinations therein. More preferably the morsels range in size from about 250 μm to about 2000 μm or 250 μm to about 1000 μm and all combinations and permutations thereof. A preferred morsel may maintain a high degree of porosity and has pore sizes over a broad distribution.

It will be appreciated that the porosity of the present invention is similar to that of inorganic shaped bodies disclosed in the '519 and '246 patents. The bone graft materials of the present invention are indeed improvements on the inorganic bodies disclosed in the '519 and '246 patents, as they are capable of being shaped into a workable mass and/or injected. For some embodiments of the present invention, the inorganic bodies of the '519 and '246 patents are modified using various natural and synthetic polymers, film forming materials, resins, slurries, aqueous mixtures, pre-polymers, organic materials, and other adjuvants. Materials such as collagen, hyaluronic acid, polylactic acid, polyglycolic acid, poly-L-lactic acid, poly-D-lactic acid, poly (L-lactide co D,L lactide), combinations of lactic/glycolic acids, wax, glycerin, gelatin, polysaccharides, polycaprolactone, polysulfone, pre-polymeric materials such as precursors to various nylons, acrylics, epoxies, polyalkylenes, and the like, were caused to permeate all or part of the inorganic bodies formed in accordance with the '519 and '246 patents. Many of the bone graft materials have improved clinical handling when compared to the bodies of the '519 and '246 patents.

The bone graft materials may also have improved handling that can provide a unit dose delivery. The addition of a polymer in the present invention graft material greatly enhances the ability of the product to be shaped, formed, or injected upon being wetted with fluids. This feature finds utility in a variety of surgical applications, particularly since the bone graft can be formed "in situ" in an operating room to suit the needs of the patient in cases where the bone void to be filled is an irregular shape. Some graft materials disclosed may also be delivered into the bony site directly, shaped, and allowed to wick bodily fluids by an operator while during an operation. Others may be injected in the site using standard delivery devices such as syringes, tubes, or the delivery devices as disclosed herein. Still other embodiments may be infiltrated with fluid in a delivery vessel to produce a shapeable mass and can be delivered without requiring hand mixing or some other touching by hand.

Figure 8A:
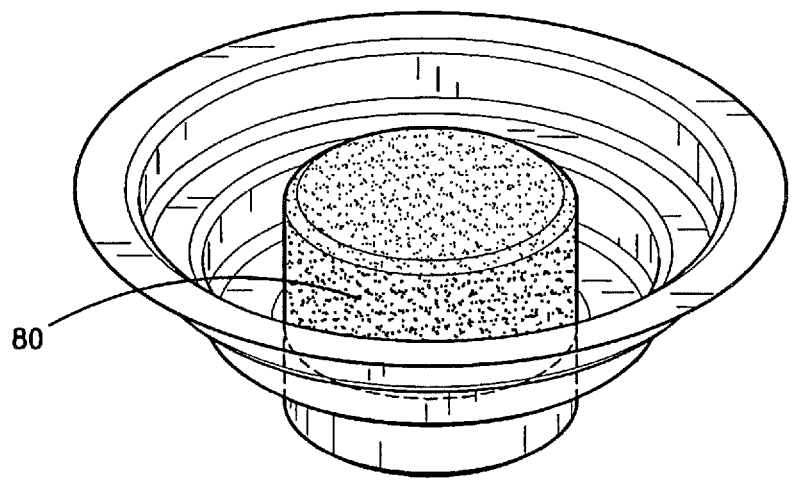
FIGS. 8A and 8B illustrates a packaging container for the present invention in which the packaging also serves as a mixing container with a cavity for receiving a predetermined amount of fluid and mixing with the graft material 80.
Figure 8B:
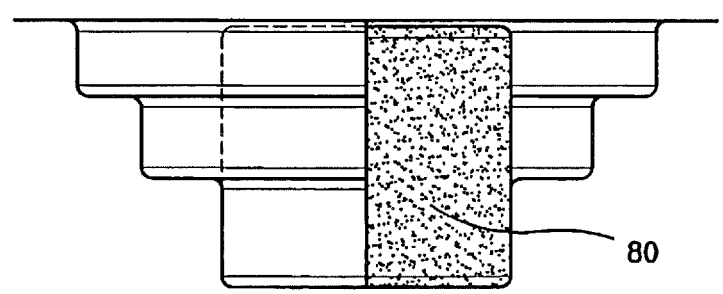

FIGS. 8A and 8B depict one embodiment of the present invention in which the bone graft material is housed in packaging that also serves as a mixing "bowl." As shown, the graft material is seated in one compartment of the inner cavity. The remainder of the inner cavity is sized to receive a predetermined amount of fluid, which, when soaked and mixed with the graft material, produces a pliable mass with optimal handling features.

Unlike materials of the prior art, the bone graft materials of the present invention are stable and, therefore, may be terminally sterilized by gamma irradiation at a range of about 25 kGy to 40 kGy. Even after sterilization, the materials are stable on the shelf for up to 1 year and preferably up to 2 years and do not require refrigeration as with other materials.

Many of the embodiments disclosed herein are used to fill bony voids and defects and may not be intrinsic to the stability of the surgical site. It will be appreciated that applications for the embodiments of the present invention include, but are not limited to, filling interbody fusion devices or cages (ring cages, cylindrical cages), placement adjacent to cages (i.e., in front cages), placement in the posterolateral gutters in posteriolateral fusion ("PLF") procedures, backfilling the iliac crest, acetabular reconstruction and revision hips and knees, large tumor voids, use in high tibial osteotomy, burr hole filling, and use in other cranial defects. Additional uses may include craniofacial and trauma procedures in which defects are frequently irregular in shape.

Due to the wide range of applications for the embodiments of the present invention, it should be understood that embodiments of the present invention graft material may be provided in a wide variety of volumes. Some embodiments can be used with other bone graft substitutes or materials, such as commercially available allograft, autograft, DBM, and synthetic products including those sold by Orthovita, Inc., Malvern, Pa., under the tradename Vitoss®.

In applications requiring graft materials with load bearing capabilities, the graft materials of the present invention may be used in conjunction with standard orthopedic hardware including meshes, plates, screws, rods, sutures, staples, cerclage wire, implants of metal, such as titanium or stainless steel, or of a polymer or composite polymer such as polyetheretherketone ("PEEK"), or nitinol.

The present invention may also be used in conjunction with orthopedic load-bearing materials such as vertebral body replacement devices and spinal implants, such that the present invention material is injected in the openings of such devices. The load-bearing frame may be made of a metal such as titanium or of a load-bearing resorbable composite such as PEEK or a composite of some form of poly-lactic acid ("PLA"). In the case of the latter, the acid from the PLA co-acts, or interacts with the calcium phosphate of the embedded bone graft material to provide an implant with superior resorption features.

In other embodiments, there is a graft for the restoration of bone in the form of a shaped body, the shaped body comprising a polymer and beta-tricalcium phosphate, the material of the graft having interconnected macro-, meso-, and microporosity; the body shape being capable of being made injectable upon wetting and injected in a volume to conform generally to a mammalian, anatomical bone structure. The amount of material used will vary depending on the area of the body being repaired.

In another embodiment of the present invention, the graft material may be shredded or cut into small pieces and placed in a syringe body. In this fashion, fluids may be directly aspirated into or injected into the syringe body thereby forming a cohesive, shapeable bone graft mass "in situ" depending upon the application requirements. The shredded pieces allow for high surface area exposure for optimal mixing with fluids to produce a cohesive injectable putty, which finds particular use as filler for irregular bone void defects and can be injected to insure maximum contact with adjacent bone for beneficial healing.

One the present invention also includes bone graft systems for the repair of bone defects containing a preformed, dry bone graft material 80, a delivery tube 10 and plunger 20 with a syringe body 30 and piston 40. Illustrative components of the systems are shown in FIGS. 5-7B. The dry bone graft material 80 has been described throughout this application and comprises a flowable body comprising about 15% to about 30% by weight, and all combinations and subcombinations therein, of biocompatible polymer, an inorganic composition comprising calcium phosphate with a size range of about 100 μm to about 4000 μm and all combinations and subcombinations therein, and said flowable body being imbibed with a fluid.

It will be appreciated that methods of treating bony defects are foreseen by the embodiments of the present invention. A method for restoring or repairing bone in an animal comprising accessing a site to be restored and injecting into a bony space a flowable bone graft material comprising biocompatible, resorbable collagen, the oxidation-reduction reaction product of at least one metal cation, at least one oxidizing agent, and at least one oxidizable precursor anion. The flowable graft material used in this method may be chosen by one skilled among those disclosed in the present application. Alternatively, a method for restoring or repairing bone in an animal comprising accessing a site to be restored; loading a syringe body with a bone graft material; mating the syringe body with a delivery tube; positioning the delivery tube at the site to be restored; using a syringe piston to advance the bone graft material into the delivery tube; and using the syringe piston and/or a plunger that mates with the delivery tube after removal of the syringe body to deliver the bone graft at a force of less than 50 lbs extrusion force wherein the bone graft material is at least 80% porous with a nominal mineral to collagen ration of 80:20. In some embodiments that may be preferred, the extrusion force may be between about 20 lbs to about 25 lbs.

EXAMPLES

Example 1

One embodiment was comprised of β-TCP, with a cation to anion ratio of $Ca_3(PO_4)_2$; and medical grade Type I bovine soluble collagen, manufactured in the following manner. Inorganic scaffolds were made using the RPR process disclosed in U.S. Pat. Nos. 5,939,039 and 6,325,987. The resultant inorganic scaffolds were crushed and sieved to obtain morsels in the size range of 0.25 mm-4 mm. The morsels were added to a soluble collagen slurry in a wet processing room and the resultant slurry was further mixed, molded, and processed in a cleanroom. The shapes were freeze-dried to produce resultant bone graft material. The shapes were in 5 cc units of bone graft material and were wetted with 2.0 cc of blood per unit and kneaded to form a putty-like mass.

Example 2

Mineral Component of Bone Graft Material

Approximately 70%-80% by weight of some bone graft materials of the present invention is β-TCP, with the cation to anion ratio of $Ca_3(PO_4)_2$. Each lot of the mineral component of these bone graft materials was tested using X-ray diffraction (XRD) to confirm phase pure β-TCP in accordance with ASTM F1088-87, Standard Specification for Beta-Tricalcium Phosphate for Surgical Implantation. In addition to XRD, Inductively Coupled Plasma Chromatography (ICP) was used to demonstrate that the levels of heavy metals in the predicate bone graft material are below those established in ASTM F-1088-87. Fourier Transform Infrared Spectroscopy (FTIR) analyses of the bone graft material were also performed.

The quantitative XRD results depicted in FIG. 9 show that the mineral component of the bone graft material is 98.15% pure β-TCP, which matches well with the ICDS standard plot for β-TCP pictured with the representative XRD pattern of the bone graft material. The ICP results for the bone graft material show that the levels of heavy metal contaminants—arsenic (As), cadmium (Cd), mercury (Hg), and lead (Pb), are below the method detection limits set forth in ASTM F-1088-87. Qualitative FTIR results show a good match of the bone graft material to β-TCP. A representative FTIR spectrum is shown in FIG. 10.

Example 3

Bulk Density

Bulk density of bone graft material was calculated from fifteen representative samples, to provide an average calculated density of 0.191 g/cc+/−0.003 g/cc.

Example 4

Porosity and Pore Size Distribution

In one embodiment of the present invention, as determined by mercury intrusion porosimetry, pore diameters in the graft range from 1 µm to 1000 µm. Approximately 50% to 65% of the pores are greater than 100 µm, approximately 15%-40% of the pores are between 10 µm-100 µm, and approximately 10%-15% of the pores are less than 10 µm. The larger macro pores (greater than 100 µm) allow bone to grow in apposition to the calcium phosphate surfaces of the implant. The smaller meso (10 µm-100 µm) and micro (less than 10 µm) interconnected pores allow for fluid communication and nutrient transport. Total porosity is approximately 80%-96%.

Example 5

Scanning Electron Microscopy Evaluation

Scanning electron micrographs (SEM) of one embodiment of the present invention graft material are provided in FIGS. 11 through 13.

Example 6

In-Situ Hands-Free Delivery

Figure 14:
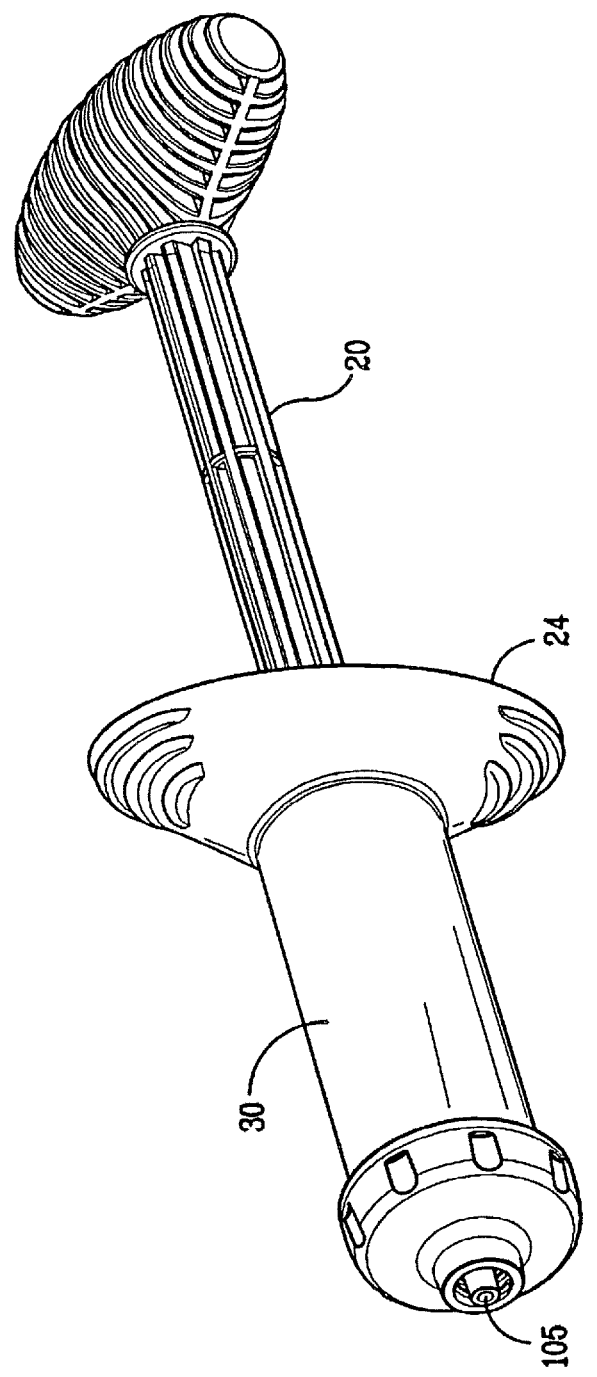
FIG. 14 illustrates a delivery device suitable for producing and delivering an injectable hands-free bone graft material.

Three 2.5 cc cylindrical bone graft units were packed into a 15 cc custom canister delivery device as shown in FIG. 14. Blood was injected into the front Luer 105 of the custom canister delivery device using a standard off-the-shelf syringe. Constant pressure was held on the front end of the custom canister delivery device using the off-the-shelf syringe and constant pressure was held on the back end of the custom canister delivery device using a custom syringe device that mated to the piston of the custom canister delivery device. After approximately 2 minutes, the bone graft material and blood formed a homogenous pliable, injectable mass.

Example 7

Extrusion Force of a Bone Graft Material

Six 2.5 cc units of gamma-sterilized bone graft material were kneaded after wetting with 12-15 cc sterile 0.9% Operating Room (OR) Grade saline. The samples easily transformed into a homogenous mixture free of any clumps within 2 minutes from the time of hydration. The samples were then tested for extrusion force. The test set-up included an Instron testing apparatus with 200 lb load cell, 10 cc custom syringe, and threaded metal funnel (ID4.5 mm, 2" long). The piston of the custom syringe was removed and the syringe was packed with 10 cc of the kneaded bone graft material. The syringe piston was re-mated with the syringe body and set in the test apparatus for testing. The test apparatus held the filled syringe body at the finger tabs of the syringe. The test apparatus insured that the longitudinal axis of the syringe body was held parallel to the applied load as the load was applied to the flat head of the piston. The load (via the crosshead) was applied at a displacement rate of 15-25 mm/min. The extrusion force was marked as the highest load measured by the load cell. On average (n=6), the maximum extrusion force was less than 20 lbs. for this test set-up.

What is claimed is:

1. A flowable body having macro-porosity, meso-porosity, and microporosity comprising:
   a homogenous mixture comprising a biocompatible polymer in the amount of about 15% to about 30% by weight and
   a material with a size range of about 100 µm to about 4000 µm comprising the oxidation-reduction reaction product of at least one metal cation, at least one oxidizing agent, and at least one oxidizable precursor anion, wherein the reaction product comprises calcium phosphate: said flowable body being imbibed with a fluid, and
   wherein homogeneous means that the porosity and pore size distribution is the same throughout the composite.

2. The flowable body of claim 1 having a porosity of about 75%.

3. The flowable body of claim 1 having a porosity of about 80%.

4. The flowable body of claim 1 having a porosity of about 90%.

5. The flowable body of claim 1, wherein said polymer comprises collagen.

6. The flowable body of claim 1, wherein said polymer comprises soluble collagen.

7. The flowable body of claim 6, wherein said soluble collagen has limited cross-links.

8. The flowable body of claim 1 comprising about 15% to about 25% by weight of biocompatible polymer.

9. The flowable body of claim 1 comprising about 15% to about 20% by weight of biocompatible polymer.

10. The flowable body of claim 1 comprising about 20% to about 30% by weight of biocompatible polymer.

11. The flowable body of claim 1, wherein said fluid is saline, bone marrow aspirate, or blood.

12. The flowable body of claim 1, wherein said fluid further comprises antibiotics, bone morphogenic proteins, or a therapeutic agent.

13. The flowable body of claim 1, wherein said reaction product comprises beta tri-calcium phosphate.

14. The flowable body of claim 1, wherein said calcium phosphate has a size range of about 250 μm to about 2000 μm.

15. The flowable body of claim 1, wherein said calcium phosphate has a size range of about 250 μm to about 1000 μm.

16. The flowable body of claim 1, wherein the flowable body has a porosity of at least 70% and wherein about 50% to about 60% of said porosity is macroporosity, about 15% to about 40% of said porosity is mesoporosity, and about 10% to about 15% of said porosity is microporosity.

\* \* \* \* \*